United States Patent
Von der Lippe et al.

(10) Patent No.: US 9,863,247 B2
(45) Date of Patent: Jan. 9, 2018

(54) FLOOR MILLING MACHINE

(71) Applicant: BOMAG GmbH, Boppard (DE)

(72) Inventors: Joern Von der Lippe, Hannover (DE); Matthias Schaaf, Koblenz (DE)

(73) Assignee: BOMAG GmbH, Boppard (DE)

( * ) Notice: Subject to any disclaimer, the term of this patent is extended or adjusted under 35 U.S.C. 154(b) by 216 days.

(21) Appl. No.: 14/899,740

(22) PCT Filed: Jun. 12, 2014

(86) PCT No.: PCT/EP2014/001603
§ 371 (c)(1),
(2) Date: Feb. 17, 2016

(87) PCT Pub. No.: WO2014/206534
PCT Pub. Date: Dec. 31, 2014

(65) Prior Publication Data
US 2016/0168991 A1    Jun. 16, 2016

(30) Foreign Application Priority Data
Jun. 28, 2013  (DE) .................. 10 2013 010 866

(51) Int. Cl.
*E01C 23/088* (2006.01)
*E21C 35/00* (2006.01)
(Continued)

(52) U.S. Cl.
CPC ............ *E21C 35/00* (2013.01); *E01C 23/088* (2013.01); *E21C 25/10* (2013.01); *G01N 3/56* (2013.01); *G01N 3/58* (2013.01)

(58) Field of Classification Search
None
See application file for complete search history.

(56) References Cited

U.S. PATENT DOCUMENTS

| 8,944,518 B2 * | 2/2015 | von Schoenebeck . E01C 23/088 299/1.5 |
| 2008/0153402 A1 * | 6/2008 | Arcona .................. B24B 7/188 451/352 |

(Continued)

FOREIGN PATENT DOCUMENTS

| DE | 102010014529 A1 | 10/2011 |
| EP | 2 161 375 A2 | 3/2010 |
| EP | 2 423 384 A2 | 2/2012 |
| WO | 03/064770 A1 | 8/2003 |

OTHER PUBLICATIONS

European Patent Office, International Search Report, International Application No. PCT/EP2014/001603, dated Aug. 26, 2014 (4 pages).
The International Bureau of WIPO, International Preliminary Report on Patentability, International Application No. PCT/EP2014/001603, dated Jan. 7, 2016 (6 pages).
Espacenet, English Machine Translation of Abstract, DE102010014529A1, Published on Oct. 13, 2011, retrieved from http://worldwide.espacenet.com (1 page).

*Primary Examiner* — John J Kreck
(74) *Attorney, Agent, or Firm* — Wood Herron & Evans LLP

(57) ABSTRACT

The present invention relates to a ground milling machine, in particular a road milling machine, a recycler, a stabilizer or a surface miner, comprising a milling drum with a milling drum width (a) extending along its rotational axis and with at least two chiseling devices, each of which comprises a chisel and a chisel holder, and a sensor device for determining wear on the at least two chiseling devices in a contactless manner, said sensor device comprising a sensor for measuring a wear parameter of the at least two chiseling devices, the sensor being movable at least over a part of the milling drum width (a) in order to set an identical measurement angle (α) and an identical position of the sensor relative to the at least two chiseling devices in order to measure the wear parameter of the at least two chiseling devices. The present invention further relates to a method for determining (Continued)

wear on the at least two chiseling devices of the ground milling machine in a contactless manner.

15 Claims, 5 Drawing Sheets

(51) Int. Cl.
*E21C 25/10* (2006.01)
*G01N 3/56* (2006.01)
*G01N 3/58* (2006.01)

(56) References Cited

U.S. PATENT DOCUMENTS

| 2012/0043401 | A1 | 2/2012 | Heusinger et al. |
| 2014/0324364 | A1 | 10/2014 | Wagner et al. |
| 2015/0054331 | A1* | 2/2015 | Berning ................ E01C 23/088 299/1.5 |
| 2015/0322634 | A1* | 11/2015 | Stock ........................ E02F 3/20 299/39.4 |

* cited by examiner

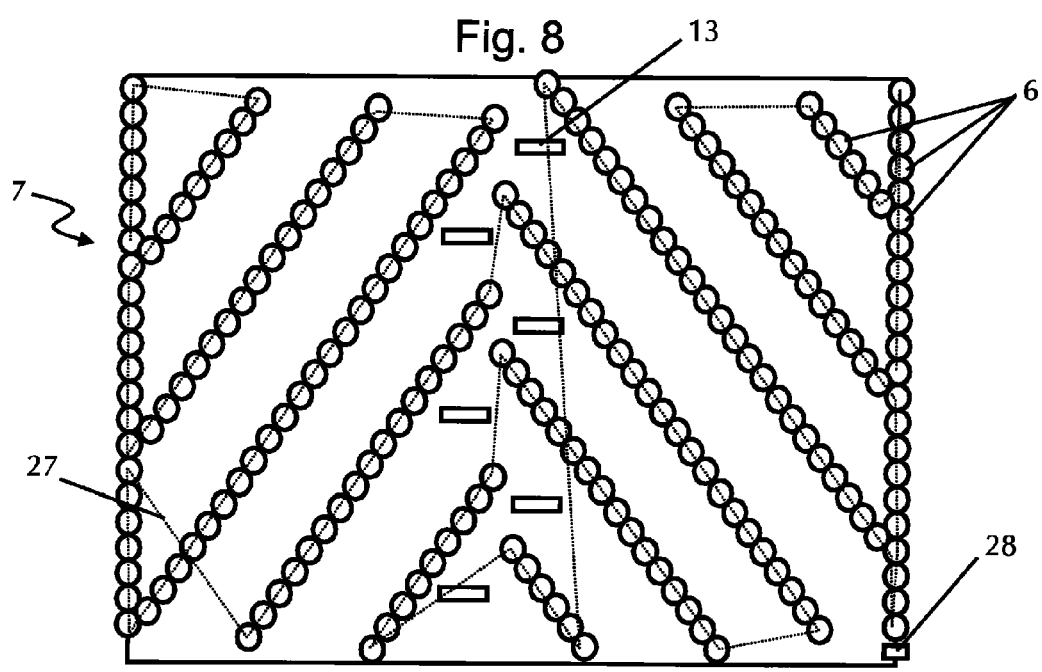
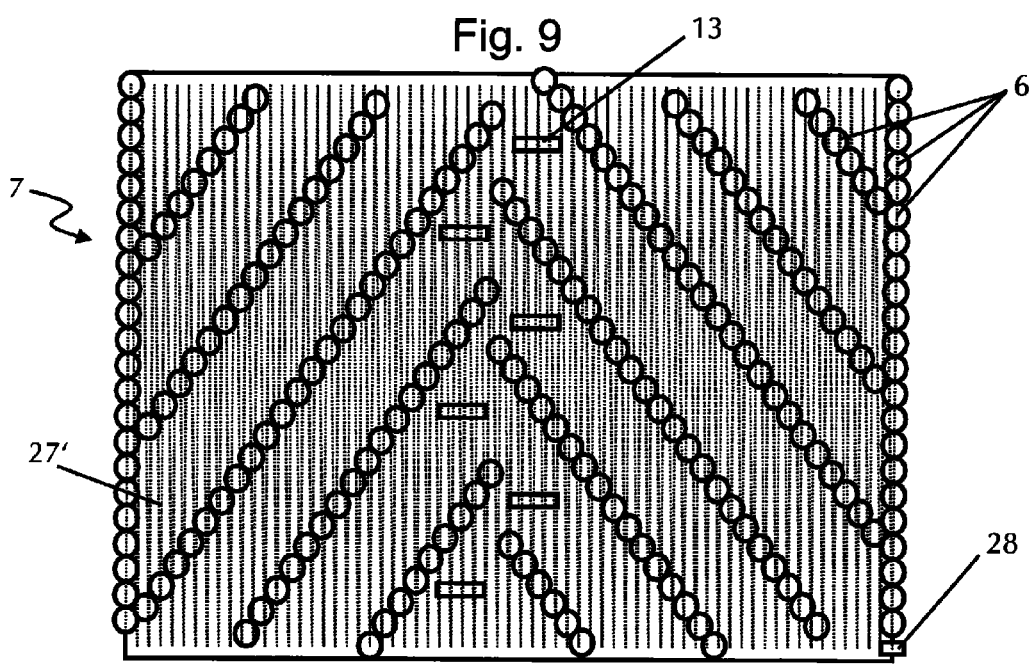

FLOOR MILLING MACHINE

CROSS-REFERENCE TO RELATED APPLICATIONS

This application is a submission under 35 U.S.C. §371 of International Application No. PCT/EP2014/001603, filed Jun. 12, 2014, which claims priority to German Application No. 10 2013 010 866.7, filed Jun. 28, 2013, the disclosures of which are hereby expressly incorporated by reference herein in their entireties.

FIELD OF THE INVENTION

The present invention relates to a ground milling machine, in particular a road milling machine, a recycler, a stabilizer, or a surface miner, comprising a sensor device for determining wear on the chiseling devices in a contactless manner. Further, the present invention relates to a method for determining wear on the chiseling devices of such a ground milling machine in a contactless manner.

BACKGROUND OF THE INVENTION

Generic ground milling machines include a machine frame, several crawler tracks, a drive motor which usually is a combustion engine, for example, a diesel engine, a work device, in particular a milling drum housing comprising a milling drum, and frequently also a discharge conveyor for transporting the milled material. Generic ground milling machines are known, for example, from EP 24 23 384 A2 for a stabilizer/recycler, and from DE 10 2010 014 529 A1 for a road milling machine.

The milling drums each are equipped with a plurality of chiseling devices which, in addition to a work tool, in particular may comprise a chisel as well as a chisel holder and/or quick-change tool holder systems. Due to a rotational movement of the milling drum, these chiseling devices will be driven into the ground during the working operation, and thereby cause the milling of the ground substrate. The processed grounds, according to the field of application of the ground milling machine, for example, can be road surfaces, stone grounds, forestal or earth grounds, etc.

Depending on the hardness of the processed ground, considerable stress on the chiseling devices may result. Due to the continuous stress on the chiseling devices, in particular on the chisel and the chisel holder, they are particularly subjected to substantial wear on heavily stressed parts. Thus, preferably, at least parts, or components, of worn-out chiseling devices will be replaced at a certain extent of wear to maintain both the performance of the ground milling machine and the quality of the milling outcome, as well as to avoid damage on other machine components such as the milling drum.

Up to now, the time point for replacing the chiseling devices usually is determined by the operator of the ground milling machine in that the operation is interrupted, the drive motor of the milling drum is deactivated and optionally uncoupled, and the chiseling devices will be checked for wear by visual inspection. This manner of checking wear, however, is time consuming, labor-intensive and, in addition, depends on a subjective assessment of the condition of the chiseling devices.

To facilitate and objectify the assessment of wear on the chiseling devices, in the prior art, furthermore, methods are known which measure the condition of the chiseling devices via sensors, and thus permit an operator-independent assessment of the degree of wear on the chiseling devices. Such a method is known, for example, from EP 2 161 375 A2, the disclosure of which is hereby incorporated by reference in its entirety. Therein, options are described to determine the position of one or more points on the surface of a chiseling device via a sensor system. In this manner, an unbiased quantification of the degree of wear on the chiseling devices can be performed. However, in the said document, for this purpose a fixed sensor is used which is to detect, from its fixed position, all chiseling devices over the entire milling drum width. In the case of a wide to very wide milling drum, it can be necessary to use several sensors which augments the production cost of the system considerably.

However, even when using a system comprising several sensors, variations in the results arise at the edge of the respective measuring range due to the different angles between the sensor and the chiseling devices. Owing to the unequal placement of the respective chiseling devices relative to the sensor, the degree of wear on various chiseling devices is detected with varying accuracy. With a different stress on individual chiseling devices, especially, significant differences in the assessment of the condition of the chiseling devices may result for this reason.

SUMMARY OF THE INVENTION

Therefore, it is the object of the present invention to improve the contactless determination of wear on the chiseling devices of a generic ground milling machine in that for each individual chiseling device of the milling drum, a determination of the state of wear is enabled in a manner as exact as possible. At the same time, the corresponding device should be comparatively cost-efficient and have a high operational reliability.

Thus, the present invention relates to a generic ground milling machine with a machine frame, a drive motor, a milling drum housing comprising a milling drum having a milling drum width which runs along its rotational axis and with at least two chiseling devices, each of which comprises a chisel and a chisel holder, and with a sensor device for determining wear on the at least two chiseling devices in a contactless manner, said sensor device comprising at least one sensor for measuring a wear parameter of the at least two chiseling devices.

According to one aspect of the present invention, said at least one sensor can be moved at least over a part of the milling drum width in order to be able to set an identical measurement angle and an identical position of the sensor relative to the at least two chiseling devices in order to measure the wear parameter of the at least two chiseling devices. Hereby, each individual chiseling device can be measured by the sensor of the sensor device under identical perspective conditions and in an identical arrangement relative to each other, respectively, independently of its respective position on the milling drum.

By spinning the milling drum around the rotational axis and by shifting or moving, respectively, the sensor along the milling drum width and in particular parallel to the rotational axis, thus, the milling drum may be adjusted with respect to almost every location on its outside jacket surface, and with respect to the at least two chiseling devices arranged on said outside jacket surface, respectively, into the identical relative position such that the at least two chiseling devices, independent of their specific location of arrangement on the milling drum, can be measured under identical perspective conditions. Hereby, a precise and, furthermore, immediate mutually comparable determination of wear of the at least two chiseling devices, and in particular of all chiseling devices present, of the milling drum is enabled.

One important aspect of the present invention, therefore, is based on the finding that, for a determination of the degree of wear of chiseling devices on a milling drum which is exact and comparable between individual measurements, there have to be identical conditions for each individual measurement of each individual chiseling device to be measured. The essentially relevant conditions include, on the one hand, the measurement angle between sensor and chiseling device which is influenced by the rotary motion of the milling drum, and, on the other hand, the position of the sensor relative to the chiseling device in axial direction of the milling drum which is different, in case of a fixed sensor such as in the prior art, for each chiseling device and which is equalized by the movability of the sensor of the present invention for all the chiseling devices. In general, the first condition, i.e., the measurement angle, more particularly, refers to the viewing angle of the sensor onto the respective chiseling device to be measured. Thus, the measurement angle is, for example, that angle which is located between the viewing direction of the sensor and, for example, the longitudinal axis of the chiseling device in radial direction relative to the rotational axis of the milling drum, and which varies in the case of a fixed sensor and a rotating milling drum. The measurement angle, inter alia, depends on the diameter of the milling drum, the exact location of the sensor within the milling drum housing, the distance of the sensor to the particular chisel to be measured, and its length. The position of the sensor relative to the chiseling device with respect to the measurement angle between the sensor and the chiseling device, therefore, is adjustable, both in the present invention as well as according to the prior art. The difference of the present invention compared to the prior art methods consists in the fact that in the present invention the second measurement condition, i.e., the position of the sensor relative to the chiseling device along the milling drum width, is adjustable.

For this purpose, the sensor can be moved parallel to the rotational axis of the milling drum along the milling drum width in both directions until it reaches a perspective view of the chiseling device to be measured which is uniform for all measurements. The measurement of the chiseling device does not occur until both of the measurement conditions are satisfied, i.e., when both the predefined measurement angle as well as the predefined adjustment position of the sensor along the milling drum width relative to the chiseling device have been attained. In the prior art, only the measurement angle can be adjusted, but not, as according to the present invention, the position of the sensor along the milling drum width, so that with chiseling devices situated more remotely to the sensor, inaccurate measurements occur which are caused partly due to the greater distance of the sensor from the chiseling devices, partly due to a perspective distortion of the chiseling devices in the viewing position of the sensor.

Using a movement of the sensor along the milling drum width, as according to the present invention, and a rotational movement of the milling drum, the identical perspective measuring conditions can be set for each chiseling device by virtue of the present invention, since, independent of the specific position of the chiseling device on the milling drum, each chiseling device can individually be measured under the same perspective conditions with respect to the relative position of the sensor and the respective chiseling device to be measured. By equalizing the measuring conditions, the measurement for each individual chiseling device has the same informativeness, and the individual measured values of the chiseling devices can be compared with another directly, independent of the specific position of the particular chiseling device on the milling drum. Differences between the values reflect different degrees of wear on the chiseling devices, and are not attributable to non-uniform measurements.

It is of particular advantage if the sensor is provided movable in parallel to the rotational axis of the milling drum. By such a movability of the sensor which is linear and, ideally, feasible at least over the entire milling drum width, it is ensured that always the identical position of the sensor relative to the respective chiseling device can be set, and after the setting of the identical measurement angle by rotating the milling drum and the corresponding shifting of the sensor along the milling drum width, for all chiseling devices, the identical measuring conditions with respect to the position of the at least one sensor relative to the respective chiseling device to be measured are present. Thus, with a movement of the sensor parallel to the rotational axis of the milling drum, there will occur no change in the distance of the sensor to the milling drum by which the uniformity of the measurements would be impaired, instead merely identical relative locations of the sensor relative to the chiseling devices are set.

Ideally, the sensor device comprises a guide means, in particular a linear guide means, along which the sensor can be moved. A linear guide means is characterized in that it moves the sensor along a guide path extending straightly, in particular parallel to the rotational axis of the milling drum. By moving the sensor along a guide means, it will be ensured that the sensor performs a predefined movement while being adjusted, in particular parallel to the rotational axis. Hereby, it is possible to set the position of the sensor relative to the milling drum and, hence, relative to the chiseling devices in an especially precise manner and, thus, to influence the measuring accuracy positively.

Principally, for the specific configuration of the guide means, a plurality of various alternatives can be used. In a particularly preferred manner, the guide means comprises a guide rail along which the sensor may be moved. The sensor can be positioned especially accurately, if it is moved on or along a guide rail for its guidance.

To be able to equalize the measurement conditions for each individual chiseling device at the milling drum, it is of advantage if the guide means extends across the complete width of the milling drum housing. Thus, the sensor can be proceeded over the complete width of the milling drum and, hence, always be moved to the identical position with respect to the milling drum width relative to the chiseling device, irrespective of at which location of the milling drum this chiseling device is located. Therefore, it is possible for each chiseling device to produce the identical perspective measurement conditions by having the sensor shifted to the corresponding position relative to this chiseling device and having the milling drum perform a rotary motion which sets a measurement angle which is identical to that used for all other measurements. Especially in the edge portion of milling drums, there are frequently more heavily stressed chiseling devices at which it is all the more important to be able to execute an exact determination of the degree of wear for being able to replace them in time. Principally, it is possible that the guide means of the sensor device extends only over a part of the milling drum housing, and hence of the milling drum width, but this has the consequence that only a part of the chiseling devices can be assessed under identical measurement conditions such that the measured values of different chiseling devices may be compared directly with each other. How large the portion across which the guide means extends and across which the sensor can be moved accordingly, should be, however, is a matter of arbitrary choice. Similarly, the portion across which the guide means extends can be chosen both at one end of the milling drum housing as well as in the center or asymmetrically within the milling drum housing with respect to the milling drum width. Considering the above-said, however, designing the guide means in such fashion that it allows for setting the sensor over the complete milling drum width is especially preferred.

Specifically, the sensor device can comprise, for example, a spindle drive, a gear rack drive or a toothed belt drive in order to move the sensor relative to the milling drum and in particular along the guide means. A spindle drive includes a spindle which basically resembles a long screw shaft, and which is guided by a thread which is attached, for example, to the sensor. The spindle is operated by a rotary motion which the thread with the sensor attached cannot follow, whereby at the sensor and the thread, a conversion of the rotary motion into a linear motion of the sensor with the thread occurs. Depending on the sense of rotation of the spindle, the sensor with the thread can be moved in two opposite directions. In a gear rack drive, the rotary motion of a pinion is transformed into a translational movement by gearing with a, especially linear, gear rack. Herein it is practical if the drive which drives the rotary motion of the pinion is disposed at the sensor or at a component supporting the sensor, respectively, and directs the interaction of the pinion, the drive and the gear rack into a linear motion of the drive and of the sensor along the gear rack. In driving the sensor by a toothed belt drive, the drive means itself, which drives the toothed belt, may be located at a different site within the ground milling machine. It is not mandatory to locate the said directly at the sensor. A sensor is attached to a toothed belt and is carried along by its movement. With the drive types described above, any occurrence of slippage is avoided, so that an accurate positioning of the sensor is made possible. Of course, the sensor also may be driven by other types of drive means, for example, belt drives, as long as these allow the controlled positioning of the sensor relative to the milling drum over the milling drum width.

For positioning the sensor relative to the chiseling devices it is optimal if a position sensor is present which detects the position of the sensor relative to the milling drum with respect to the milling drum width. In other words, at any time during the operation of the sensor device, by means of the measurement of a position sensor, it should be known at which location the sensor is situated within the milling drum housing, in particular with respect to the milling drum width. This information is important for both a positioning of the sensor relative to the respective chiseling devices and an exact determination of the degree of wear as well as for the identification of the respective chiseling devices by assigning them to their positions on the milling drum. Here, position sensors are conceivable which determine the position of the sensor absolutely or also relatively, for example, by use of rotational values in a drive means or at a spindle. If the sensor is driven by a spindle drive, the position sensor, for example, can measure the rotation of the spindle and derive the position of the sensor on the guide means therefrom.

Because in this case the position sensor is one which performs a relative measurement, it is necessary, after losing information about the absolute position of the sensor, for example, due to a restart of the machine, to determine the absolute position again. For this purpose, for example, a switch can be disposed at one end of the guide means, towards which the sensor has to be moved at the start of the measuring process until it will actuate said switch, and thus its position can be determined. With absolutely measuring position sensors, for example, wire rope sensors, this is not necessary.

The specific manner of the position determination of the position sensor does not matter, it is merely important that the position of the sensor during its movement along the milling drum width is determined. Where exactly the position sensor will be arranged, amongst other things, also depends on the drive type. With spindle drives, the position sensor, for example, does not have to be arranged directly at the sensor, but may be arranged outside the milling drum housing, which is space-saving. In case of a gear rack drive which is arranged directly at the sensor or at least is moved together with the said, the position sensor can also be directly arranged at the sensor or at an element supporting the sensor.

The sensor device being a costly and sensible component, it is preferred if a protective device for the sensor device is provided for protecting the sensor device from damages, in particular those inflicted by milled material. Ideally, said protective device is adjustable between a protected position in which the protective device covers the sensor device at least partially, and a release position in which it exposes the sensor device in such a manner that the sensor is able to measure the chiseling device.

For example, this can be achieved in particular by configuring the protective device, or at least a part of it, such that it can be moved together with the sensor device. A concerted movement of the sensor device together with the protective device allows for keeping the sensor in a protected position during operation of the ground milling machine, and, thereafter, for determining the state of wear on the chiseling devices, for moving it into a measurement position which compared to the protected position is closer to the milling drum and, hence, to the chiseling devices. This shortening of the distance between the sensor and chiseling device by the concerted movement of the protective device and the sensor device increases the precision of the wear determination. This increased precision, by virtue of the shortening of the distance from the sensor to the milling drum, is associated with a decrease of the measuring range of the sensor which however is uncritical due to the movability and adjustability, respectively, of the sensor according to the present invention.

In particular for protecting the sensor device it is also advantageous if a control device is provided which prevents that the sensor device leaves its protected position during the milling operation. If, during the operation of the ground milling machine, it should erroneously be attempted to carry out a measurement of the wear parameter of the chiseling devices, then releasing the sensor device out of its protected position with the milling drum rotating in working operation would possibly cause damage to the sensor device, either by the milling drum itself or by milled material flying around. Therefore, it is advantageous if prior to each release of the sensor device out of the protected position into the measuring position, it is checked by a control device whether the milling drum is in working operation, and if so, the release of the sensor device out of its protected position is prevented. Only for the case that the ground milling machine, and hence the milling drum, is not in working operation, the control device will allow the release of the sensor device out of its protected position for measuring the wear parameter of the chiseling devices. Hereby, damage to the sensor device due to operator errors or device faults are avoided.

Independent of the above-described protective device, it is principally advantageous if the sensor device is disposed such that, in order to measure the wear parameter of the chiseling devices, it can be moved into the milling drum housing, and after completion of the measurement out of the said again. In this way it is possible to utilize the advantages of a shortening in the distance between sensor and milling drum, as described above, and simultaneously avoid any negative impairment of the flow characteristics of the milled material within the milling drum housing during working operation of the ground milling machine by the sensor device.

Further, the object is achieved by a method for determining wear on chiseling devices of a ground milling machine of the type described above in a contactless manner, comprising a measurement of a wear parameter of the at least two chiseling devices, wherein, according to the present invention, a movement of the sensor at least over a part of the milling drum width is provided in order to set identical perspective measurement conditions regarding measurement angle and position relative to the respective chiseling device to be measured with respect to the milling drum width between the sensor and the at least two chiseling devices, in order to measure the wear of at least two chiseling devices.

The method according to the present invention is based on the same considerations and findings which have been described for the ground milling machine according to the present invention as described above. One aspect of the present invention is to enable an equalization of the measurement conditions (measurement angle, which can be influenced by the rotation of the milling drum, and arrangement of the sensor relative to the respective chiseling device to be measured in direction of the milling drum width, which can be influenced by movement according to the present invention of the sensor) during the measurement of each chiseling device to be measured, in order to be able to measure the chiseling devices to be measured independently of their position on the milling drum under identical perspective proportions of said one sensor with regard to a parameter relevant for the wear of the chiseling device.

An advantageous refinement of the above-described method consists in that the relative position of the sensor on a path extending parallel to the rotational axis of the milling drum and/or the rotational position of the milling drum is recorded by at least one position sensor for identifying the chiseling devices. Therein, the rotational position of the milling drum, for example, can be determined as angular displacement with respect to an initial pivot position or zero position, respectively, in a plane perpendicular to the rotational axis of the milling drum. From the relative position of the sensor with respect to the milling drum width which corresponds to the adjustment- or displacement position, respectively, of the sensor, and the rotational position of the milling drum which corresponds to the measurement angle, an identification of each individual chiseling device can be derived. Thereby, each chiseling device can be correlated with the corresponding measured value of the wear parameter determined by the sensor, whereby a differentiated wear profile of all chiseling devices of the milling drum can be produced. Thus, individual chiseling devices can be identified whose wear deviates from that of the other chiseling devices.

The measurement of the wear parameter can be carried out in an especially time-saving manner if the sensor and the milling drum, for measuring the wear parameter of the chiseling devices, are moved such that the measuring sequence of the chiseling devices corresponds to the shortest possible path between the chiseling devices. Herein, 'path' either denotes a movement path, in particular of the sensor along its adjustment trail, and/or of the milling drum about the rotational axis and/or the travel distance for connecting the chiseling devices to be measured on the milling drum, in particular when regarded in a developed view of the milling drum in a plane. Thus, for example, it is possible to shift the sensor along the milling width from the one side in axial direction of the milling drum to the other side, and to let the milling drum rotate several times about the rotational axis in the meantime. In doing so, the sensor detects the respective chiseling device which is passed along said sensor under the desired perspective conditions by the rotating milling drum. Thus, in the method, for measuring all chiseling devices present, the sensor is moved across the width of the milling drum once, and it is simultaneously rotated about the rotational axis for several times. Alternatively, the milling drum also can be rotated about its rotational axis by 360° only once, and, in exchange, the sensor can be moved to the required respective positions along the milling drum width.

Therefore, in the method, the milling drum takes the shortest travel path, specifically by 360° for one time about its own rotational axis, and the sensor is moved to the required respective position accordingly. The measuring process will be even more rapid and efficient if the sensor and the milling drum are moved such that the measuring sequence of the chiseling devices corresponds to the shortest possible connecting path of the chiseling devices on the milling drum.

In other words, the chiseling devices of the milling drum are scanned by the sensor in that sequence which corresponds to the pattern of the arrangement of the chiseling devices on the milling drum. For this purpose, it is necessary that the sensor can be moved in both directions with respect to the rotational axis of the milling drum, ideally over the milling drum width, and also that the milling drum can be moved in both rotational directions.

By virtue of the movement of the sensor and the milling drum, thus, the scanning pattern will be matched to the pattern of the chiseling devices on the milling drum. For this purpose, it can be provided, for example, that this process is coordinated and controlled by an appropriate control device, in which, for example, also the arrangement patterns of the chiseling device on the milling drum may have been stored.

Further it is of advantage if an identification of the chiseling devices is accomplished, in a similar way to a two-dimensional coordinate system, by having a combination of the rotational position of the milling drum, i.e., the rotational angle, and the adjustment position of the sensor along the milling drum width assigned to each position of a chiseling device on the milling drum. Since the location of each individual chiseling device on the milling drum is known, and each individual chiseling device may be related unequivocally to one position of the sensor and one rotational position of the milling drum, it is possible to perform the determination of wear only for certain groups of chiseling devices or even individual chiseling devices. Hereby, it is possible to check chiseling devices having increased wear selectively, without having to check all chiseling devices. For example, it may be the case that only a part of the milling drum width contacts soil material during a milling procedure, which leads to selective wear on the chiseling devices of this region. It is also conceivable to perform the measurement of the wear parameter only on distinct chiseling devices, and to utilize the measured results as indicators for the degree of wear of all chiseling devices.

BRIEF DESCRIPTION OF THE DRAWINGS

The present invention will be described in more detail below with reference to the exemplary embodiments shown in the figures. In the schematic figures:

FIG. 8 is a developed view of a milling drum with a measuring sequence of the chiseling devices; and FIG. 9 is a developed view of a milling drum with an alternative measuring sequence of the chiseling devices.

Identical parts or parts having the same functionality, respectively, are indicated by identical reference numerals in the figures wherein component parts reoccurring in the figures are not identified separately in each individual figure.

DETAILED DESCRIPTION OF THE INVENTION

Figure 1:
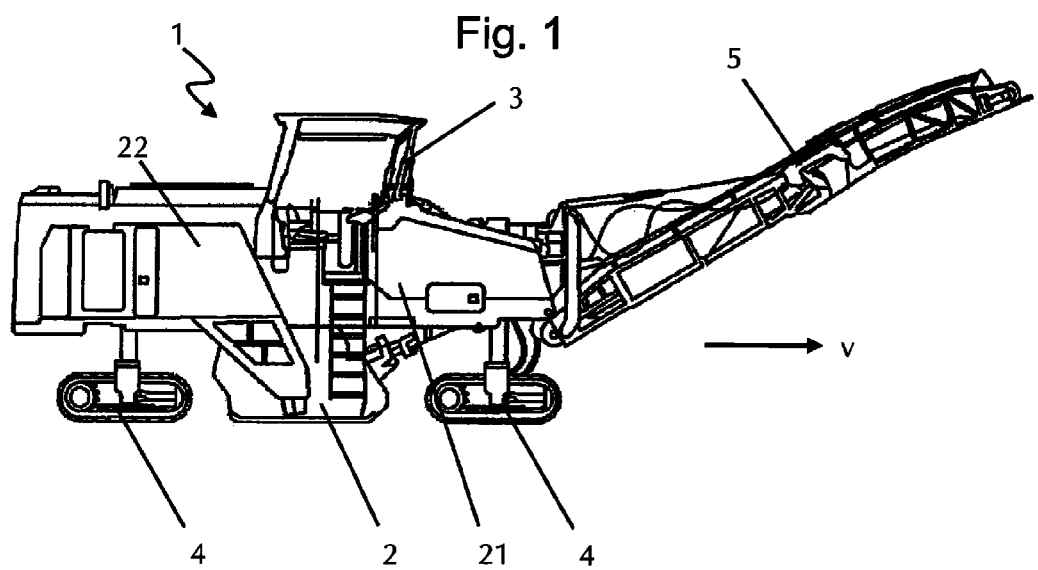
FIG. 1 is a side view of a generic ground milling machine.

FIG. 1 shows an example of a generic ground milling machine 1, more particularly a road milling machine, having a machine frame 21, crawler tracks 4, an operator platform 3, a discharge conveyor 5, a drive motor 22 and a milling drum housing 2. During the milling or working operation, the ground milling machine 1 travels in the working direction v over the soil surface to be processed, and in doing so, removes subsoil material in a predefined milling depth.

Figure 2:
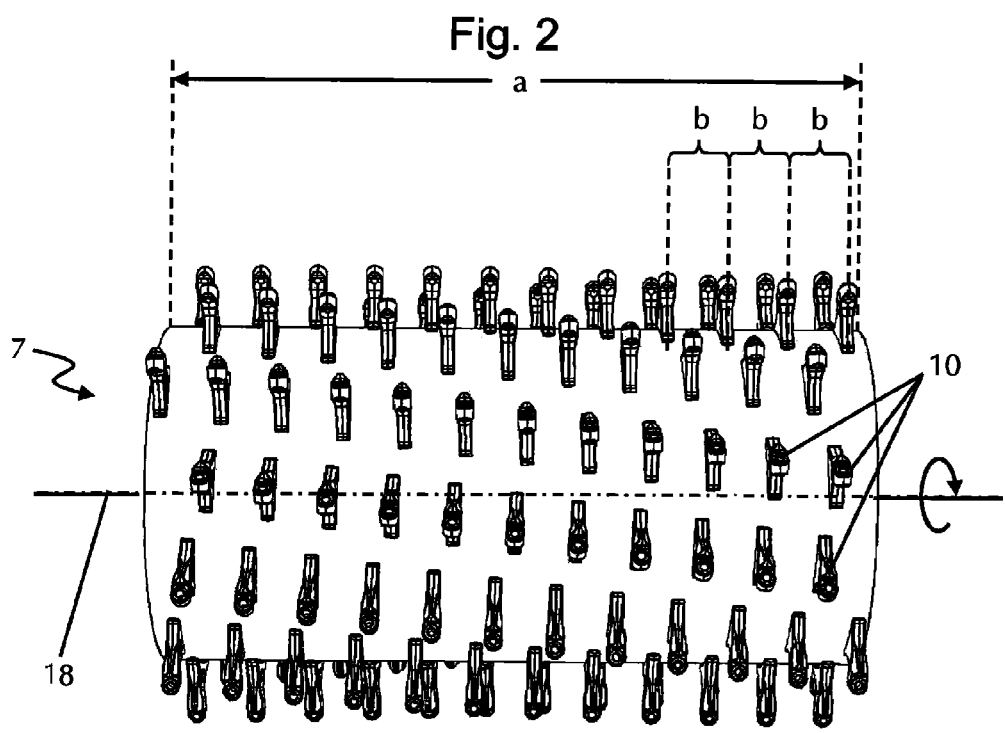
FIG. 2 is a plan view of a milling rotor with chiseling devices.

In FIG. 2, a milling drum 7 is shown, for example, as it is situated within the milling drum housing 2 of the ground milling machine 1 of FIG. 1. The milling drum 7 comprises a plurality of chiseling devices 6, wherein each chiseling device has one chisel 9, one chisel holder 10 and one quick-change holder 20 in a manner known per se. Depending on the field of use of the milling drum 7, the chiseling devices 6 are arranged in a pattern on the outside jacket surface of the milling pipe of the milling drum 7. The arrangement pattern of the milling drum 7 of FIG. 2, for example, comprises an arrangement of individual chiseling devices 6, of which, in FIG. 2, only the chisel holders 10 are indicated, in rows helically running around the rotational axis 18. Within these, the chisel holders 10 are spaced to each other at an interval b, with rows arranged consecutively in the rotational direction have an axial offset of the chiseling devices 6. The milling drum 7, in terms of its spatial dimensions, is defined by its diameter radially to the rotational axis 18 (for example, with respect to the cutting circle of the milling drum) and its milling drum width a, i.e., its extension in the axial direction of the rotational axis 18. In working operation of the ground milling machine 1, the milling drum 7 rotates about its rotational axis 18. Due to of the rotation of the milling drum 7 and the travelling of the ground milling machine 1 in the working direction v, the chisels 9 are driven into the soil and remove the same. Depending on the soil's hardness, considerable wear on the chiseling devices 6 may occur.

Figure 3:
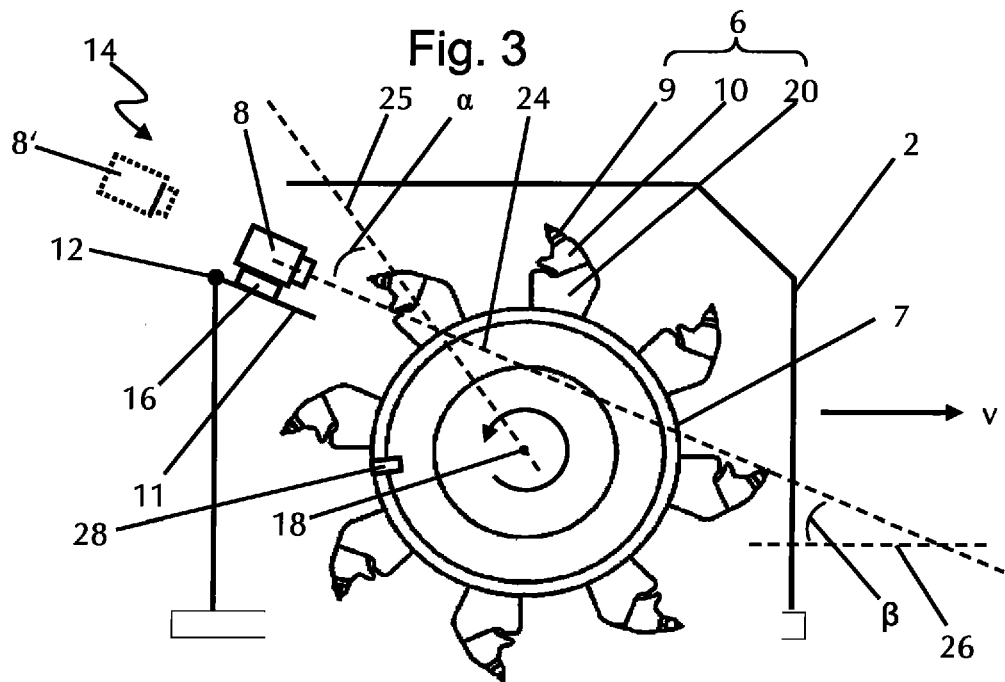
FIG. 3 is a side view of a milling drum housing with the outside cladding detached, having milling drum and sensor device in the measurement operation.
Figure 4:
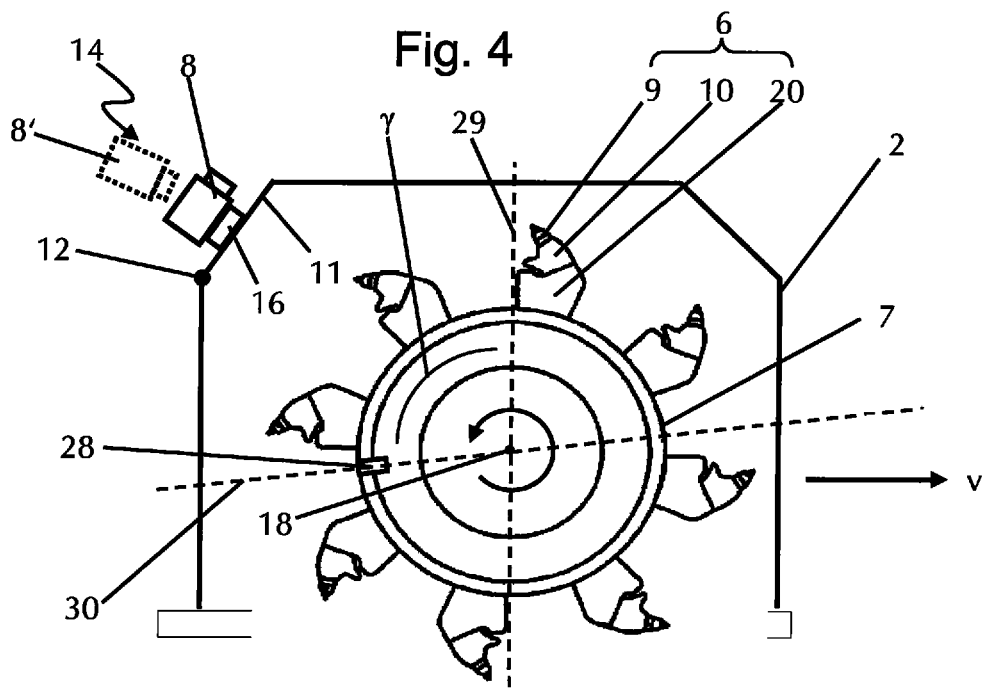
FIG. 4 is a side view of a milling drum housing with the outside cladding detached according to FIG. 3, with the sensor device in protected position.

In FIG. 3, a milling drum housing 2 and a milling drum 7 are shown in a side view with detached outside cladding. In this exemplary embodiment, the milling drum 7 comprises a chiseling device 6 which consists of a chisel 9, the chisel holder 10 and a quick change holder 20. FIG. 3 also shows a sensor device 14 in measurement mode which consists of a sensor 8 and a guide means 16. The sensor device 14 is mounted on a protective device 11 which is connected with the milling drum housing 2 via a joint 12. Via the joint 12, the sensor 8, the guide means 16 and the protective device 11 can be moved in a concerted manner. Specifically, they can be shifted out of the milling drum housing 2 by a flapping movement at the joint 12 in such a manner that only the protective device 11 is still in contact with the interior of the milling drum housing 2. This situation is illustrated in FIG. 4 which shows the sensor device 14 in working operation of the milling drum 7. An alternative arrangement of the sensor (shown by the dashed line) is indicated by 8'. In this alternative embodiment 8', the sensor is not connected with the protective device 11, but is arranged outside of the milling drum housing 2. Only the protective device 11 performs a movement via the joint 12, and either moves into the protective position covering the sensor 8' or into the measurement-position out of the sensor's measuring range. Both the sensor 8 and the sensor 8' are mounted so as to be able to move in the longitudinal direction parallel to the rotational axis 18. Moreover, the FIG. 3 shows the viewing direction 24 of the sensor 8, the central axis of which, at a sensor angle β, intersects with a line 26 parallel to the soil to be processed by the ground milling machine 1. This sensor angle β remains constant over the whole duration of measuring the wear parameters of all chiseling devices 6 to be measured.

The measurement angle α which is set by the rotary motion of the milling drum 7, lies between the central axis of the viewing direction 24 of the sensor 8 and the radial axis 25 of the chiseling device 6 which extends through the rotational axis 18 of the milling drum and the center of the base area of the chiseling device 6. The uniformity of this angle α during the measurement of each individual chiseling device 6 is achieved solely by the adjustment of the rotational position or of the current rotational angle of the milling drum 7, respectively. The measurement angle α also can be defined between the straight line 24 in the viewing direction of the sensor 8 and a straight line other than the radial axis 25 of the chiseling device 6 according to FIG. 3. Thus, it would be possible, for example, to define the measurement angle α as situated between the straight line 24 and a straight line which, starting from the rotational axis 18 of the milling drum 7, radially intersects or is tangent to any one point of the chiseling device 6, as long as for all chiseling devices 6 the same point situated on them in each case is used. It is solely of importance that the measurement angle α provides a clearly defined rotational position of the milling drum 7 relative to the sensor 8 which ensures that all chiseling devices 6 are measured from the identical perspective as regarded from the sensor 8. The measurement angle α is determined by determining the rotational angle of the milling drum 7 via a sensor 28 for the rotational position or rotational angle, respectively.

The rotational position of the milling drum 7 can be determined absolutely as well as in relation to a reference. For example, the central axis 24, the viewing direction of the sensor 8, a horizontal line 26 or the direction of the vertical line 29 might be possible. From the reference and the radial axis 30 of the rotational position sensor 28, the rotational angle γ of the milling drum 7 can be determined. Since the arrangement of the chiseling devices 6 with respect to the milling drum 7, and thus the radial axes 25 of the chiseling devices 6, are known, the measurement angle α can be determined from the rotational angle γ of the milling drum 7.

Figure 5:
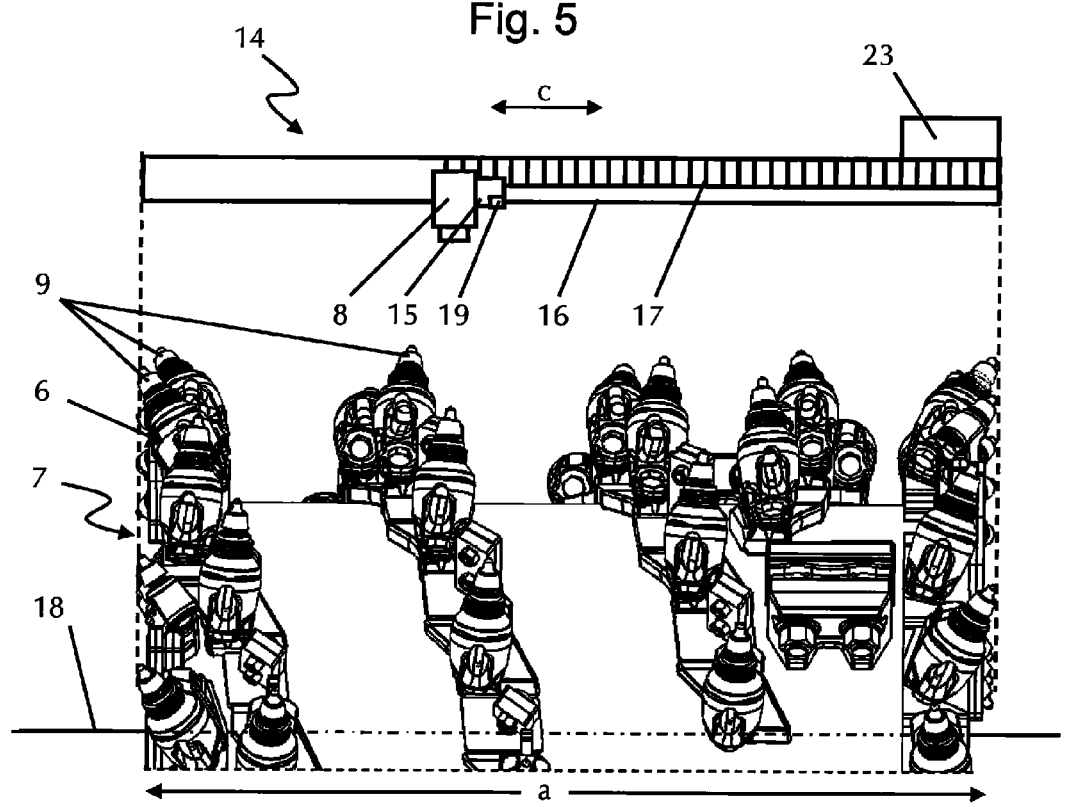
FIG. 5 is a plan view of a sensor device.

The second measurement condition which is to be identical in each measurement of each distinct chiseling device 6 is the position of the sensor relative to the milling drum width a, and is illustrated by FIG. 5 in more detail. FIG. 5 shows a movable sensor device 14. At the sensor 8, a drive means 15 and a position sensor 19 are disposed such that the sensor 8 can be displaced in the direction of arrow c parallel to the rotational axis 18 of the milling drum 7 over the milling drum width a. Together with this, the sensor 8 can be moved via the guide means 16. All ports for the drive means 15, the position sensor 19, and the sensor are provided with cables which are led by the drag chain 17. Further, a control device 23 for the control of the sensor device 14 is provided. The sensor 8, the drive 15 and the position sensor 19 can be moved via the guide means 16 such that the sensor 8 can assume any position along the milling drum width a. The sensor 8, for example, can be moved by exactly the distance b at a time, between the chiseling devices 6 along the milling drum width a. Hereby, in addition to appropriate rotation of the milling drum 7 (in the measurement mode, for example, via the drive transmission and/or a drive means especially provided for this purpose) it is possible to set the position of the sensor 8 relative to each chiseling device 6 in an identical manner. Thus, each chiseling device 10 can be measured under identical perspective conditions by the sensor 8 in terms of its wear which, in particular, facilitates the comparison of the wear of distinct chiseling devices considerably.

Figure 6:
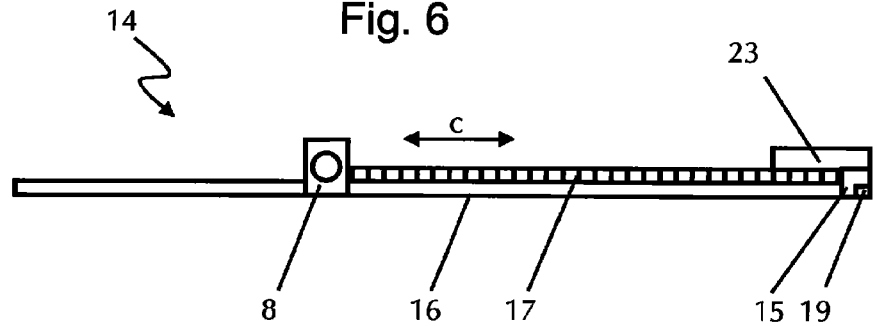
FIG. 6 is a front view of a further embodiment of a sensor device.

FIG. 6 shows an alternative embodiment of the moveable sensor device 14 according to FIG. 5. In contrast to the embodiment shown in FIG. 5, here, the drive 15 and the position sensor 19 are not directly located at the sensor 8 but at the edge portion of the guide means 16. The specific manner in which the position sensor 19 functions depends on the type of the drive 15. The position sensor 19 can measure the absolute position of the sensor 8 as well as derive the position of sensor 8 from the degree of displacement of a drive 15. The drive 15 can, for example, be a spindle drive which moves the sensor 8 along the guide means 16 by the rotation of a spindle. In this case, by quantifying the rotary motion of the spindle of the drive 15, a position sensor 19 can determine how far and in which direction the sensor 8 has moved along the guide means 16 in the direction of arrow c. For this, however, it is necessary that a starting position of the sensor 8 is known. To determine this starting position, provision can be made when starting the measurement operation to move the sensor 8 to one end of the guide means 16 at which the entry of said sensor 8 is detected by it actuating a switch. From this zero position, then, the relative movement of the sensor 8 along the guide means 16 could be calculated by a position sensor 19. It is also possible to detect the position of the sensor 8 by using other arrangements of position sensors.

Figure 7:
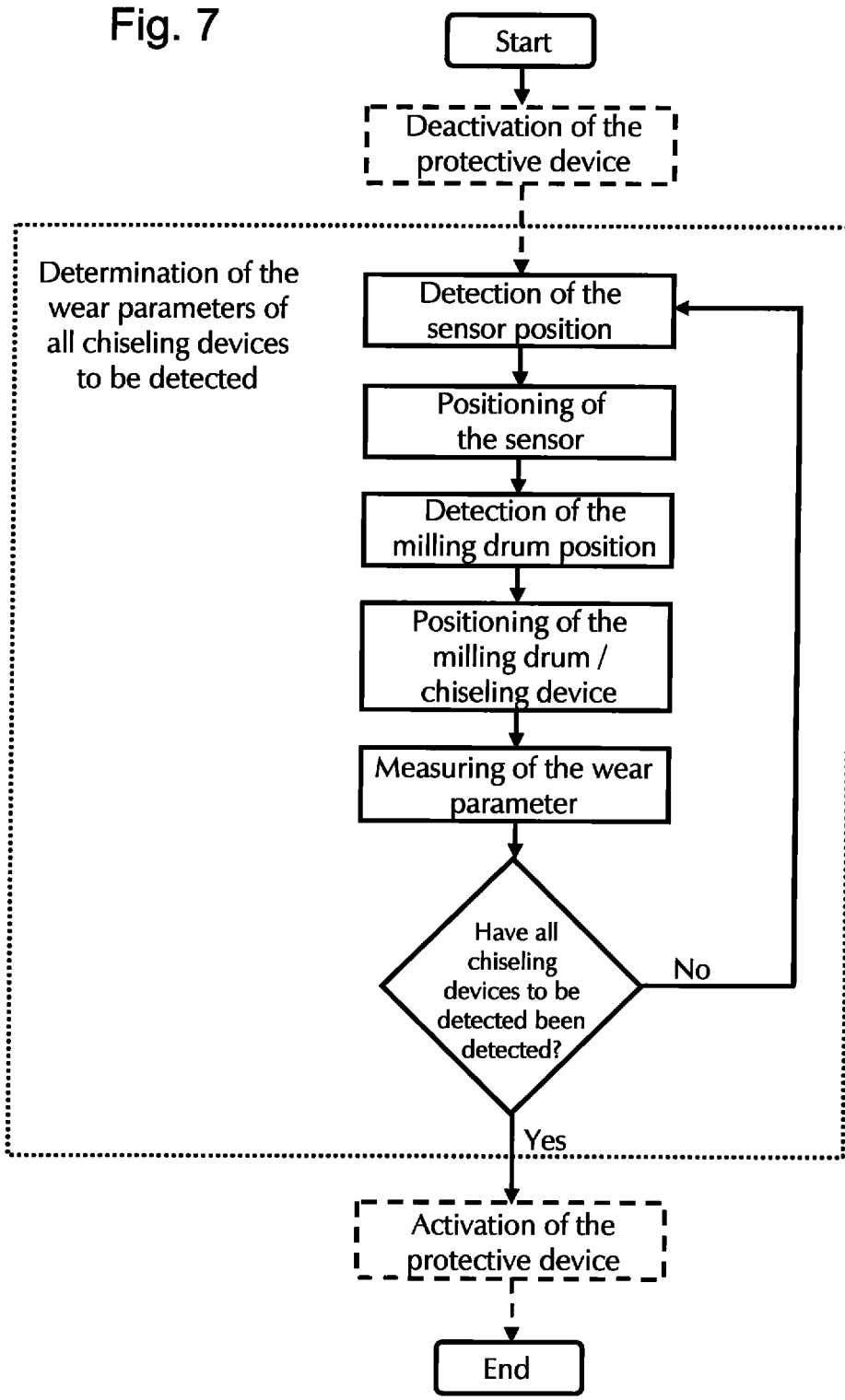
FIG. 7 is a flow chart for the sequence of the method.

FIG. 7 illustrates the sequence of the method for determining of wear on chiseling devices 6 in a contactless manner. The procedure begins when the sensor device 14 is activated. At first, optionally, a deactivation of the protective device 11 is carried out. In this step, also, a potential movement of the sensor device 14 into the milling drum housing 2 is carried out. Thereafter, the determination of the wear parameters of all of the chiseling devices 6 to be detected begins. Initially, the sensor position has to be detected if it is not already known. Then, the positioning of the sensor 8 relative to the milling drum width a is carried out. Subsequently, the rotational position of the milling drum 7 is detected if it is not already known, and the positioning of the milling drum 7 or the chiseling device 6, respectively, relative to the viewing direction 24 of the sensor 8 is carried out such that the measurement angle α is set which is identical for all measurements of all chiseling devices 6. Of course, these steps may also be performed in a different order. For example, the detection of the milling drum's rotational position and its positioning can be executed first and, thereafter, the detection of the sensor position and the positioning of the sensor 8 are performed. Just as well, it is also possible to have these processes performed simultaneously. It is only important that, at the end of these steps, the identical measurement conditions for the chiseling devices 6 to be measured are set. Thereafter, the measurement of the wear parameter by the sensor 8 is carried out. After this measurement, the control device 23 checks if all the chiseling devices 6 to be detected have been measured, and thus whether the measurement is completed. If further chiseling devices 6 are still to be measured, the position of the sensor 8 and the rotational position of the milling drum 7 are detected again, and the sensor 8 and the milling drum 7 are positioned relative to the next chiseling device 6 to be measured. This procedure is repeated until all chiseling devices 6 to be detected have been detected. At this point, the values of the wear parameter for all chiseling devices 6 to be detected are known. The measurement is finished, an activation of the protective device 11 is optionally carried out, which potentially also includes a movement of the sensor device 14 out of the milling drum housing 2. Thereby, the process is completed.

FIG. 8 and FIG. 9 each show a developed view of the outside jacket surface of the milling drum 7 which demonstrate the distribution pattern of the chiseling devices 6 schematically, which in the present case is typical for a milling drum for a road milling machine. The individual chiseling devices 6 are depicted as circles. Moreover, ejectors 13 are provided, which convey the milled material out of the milling drum housing 2 into a discharge chute. Also at the milling drum 7, there is disposed a rotational position sensor 28 for determining the rotational angle γ of the milling drum 7. Further, two different scanning patterns, or measuring schedules, are indicated by the dotted lines 27 and 27', which indicate the measurement sequence at the various chiseling devices 6 by the sensor 8. In FIG. 8, the scanning pattern 27 follows the distribution pattern of the chiseling devices 6 on the milling drum. Thus, to be able to follow the scanning pattern 27, the sensor 8/8' has to be moved in both directions along the direction of the arrow c parallel to the rotational axis 18 of the milling drum 7, and the milling drum 7 has to be moved in both rotational directions about the rotational axis 18. It is intended for these scanning patterns that the total path for scanning all chiseling devices 6 is the smallest one with regard to the chiseling devices 6. Alternatively, in FIG. 9, a scanning pattern is used, in which both the sensor 8, 8' and the milling drum 7 are moved or rotated, respectively, in one direction only. Specifically, according to FIG. 9, the sensor 8, 8' is moved in small intervals along the milling drum width a, while the milling drum 7 performs one full revolution for each interval. During this rotation, the sensor 8, 8' measures all the chiseling devices 6 relative to which, during the rotation of the milling drum 7, the sensor 8, 8' assumes the position which should be present in all measurements. Then the sensor 8, 8' is progressed by one interval, and one further revolution of the milling drum 7 is performed. Thus, the measurement of the chiseling devices 6 is performed in such a manner herein that, with respect to the movement of the sensor 8, 8' which, in summation, is shifted over the entire milling drum width only once, the smallest path is taken in order to measure all the chiseling devices 6. Alternatively, it would also be possible to rotate the milling drum 7 in intervals and to let the sensor 8, 8', for every interval, scan the complete or at least the respectively required milling drum width a, with the wear parameters of those chiseling devices 6 being measured which during this rotational setting of the milling drum 7, assume the measurement angle α which has to be present in all measurements. Accordingly, with this alternative, not shown in the figures, the shortest path would be traveled in terms of the rotary motion of the milling drum which, correspondingly, would be turned once by 360° for a measurement of all chiseling devices 6, with the sensor 8, 8' being moved to the respective relevant measuring locations with regard to the milling drum width.

While the present invention has been illustrated by description of various embodiments and while those embodiments have been described in considerable detail, it is not the intention of Applicants to restrict or in any way limit the scope of the appended claims to such details. Additional advantages and modifications will readily appear to those skilled in the art. The present invention in its broader aspects is therefore not limited to the specific details and illustrative examples shown and described. Accordingly, departures may be made from such details without departing from the spirit or scope of Applicants' invention.

What is claimed is:

1. Ground milling machine, comprising:
a machine frame;
a drive motor;
a milling drum housing;
a milling drum with a milling drum width (a) extending along its rotational axis and with at least two chiseling devices, each comprising a chisel and a chisel holder; and
a sensor device for determining wear on the at least two chiseling devices in a contactless manner, comprising a sensor for measuring a wear parameter of the at least two chiseling devices,
wherein the sensor can be moved at least over a part of the milling drum width (a) in order to set an identical measurement angle (α) and an identical position of the sensor relative to the at least two chiseling devices in order to measure the wear parameter of the at least two chiseling devices.

2. The ground milling machine according to claim 1, wherein the sensor can be moved parallel to the rotational axis of the milling drum.

3. The ground milling machine according to claim 1, wherein the sensor device comprises a guide device along which the sensor can be moved.

4. The ground milling machine according to claim 3, wherein the guide device comprises a guide rail along which the sensor can be moved.

5. The ground milling machine according to claim 3, wherein the guide device extends over the entire width of the milling drum housing.

6. The ground milling machine according to claim 1, wherein the sensor device comprises a drive, in particular a spindle drive, a gear rack drive or a toothed belt drive, for moving the sensor relative to the milling drum.

7. The ground milling machine according to claim 1, wherein the ground milling machine includes a position sensor which detects the position of the sensor relative to the milling drum with respect to the milling drum width (a).

8. The ground milling machine according to claim 1, wherein a control device is provided which prevents that the sensor device leaves a protected position during the milling operation.

9. The ground milling machine according to claim 1, wherein a protective device for the sensor device is provided, and that the protective device is moveable together with the sensor device.

10. The ground milling machine according to claim 1, wherein the sensor device is mounted such that for measuring the wear parameter of the chiseling devices, the sensor device is moveable into the milling drum housing, and after completion of the measurement, out of the same again.

11. The ground milling machine according to claim 1, wherein the ground milling machine comprises one of a road milling machine, a recycler, a stabilizer or a surface miner.

12. A method for determining wear on chiseling devices of a ground milling machine according to claim 1, in a contactless manner, comprising a measurement of a wear parameter of the at least two chiseling devices,
wherein a movement of the sensor at least over a part of the milling drum width (a) in order to set an identical measurement angle (α) and an identical position of the sensor relative to the at least two chiseling devices for measuring the wear parameter of the at least two chiseling devices.

13. The method according to claim 12, wherein the position of the sensor and/or the rotational position of the milling drum is detected by at least one position sensor for identifying the chiseling devices.

14. The method according to claim 12, wherein for measuring the wear parameter of the chiseling devices, the sensor and the milling drum are moved such that the measuring sequence of the chiseling devices corresponds to the shortest possible path between the chiseling devices.

15. The method according to claim 12, wherein an identification of the chiseling devices is carried out by having a rotational position of the milling drum and a position of the sensor along the milling drum width (a) assigned to each position of a chiseling device on the milling drum.

* * * * *